United States Patent
Chen et al.

(10) Patent No.: US 7,823,533 B2
(45) Date of Patent: Nov. 2, 2010

(54) STENT FIXTURE AND METHOD FOR REDUCING COATING DEFECTS

(75) Inventors: Yung-Ming Chen, Cupertino, CA (US); Allan Bradshaw, Newark, CA (US); Philip C. Foreman, San Jose, CA (US); Greg Teaby, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1065 days.

(21) Appl. No.: 11/174,195

(22) Filed: Jun. 30, 2005

(65) Prior Publication Data

US 2007/0003688 A1 Jan. 4, 2007

(51) Int. Cl.
*B05C 13/00* (2006.01)
(52) U.S. Cl. ............... 118/500; 118/504; 118/505; 606/1; 606/108
(58) Field of Classification Search ............ 118/500, 118/504, 505; 427/2.24, 2.25, 2.28, 2.3; 606/1, 108
See application file for complete search history.

(56) References Cited

U.S. PATENT DOCUMENTS

| | | | |
|---|---|---|---|
| 2,072,303 A | 3/1937 | Hermann et al. |
| 2,386,454 A | 10/1945 | Frosch et al. |
| 2,845,346 A | 7/1958 | Scanlon et al. |
| 3,016,875 A | 1/1962 | Ballentine, Jr. et al. |
| 3,773,737 A | 11/1973 | Goodman et al. |
| 3,827,139 A | 8/1974 | Norteman |
| 3,849,514 A | 11/1974 | Gray, Jr. et al. |
| 3,882,816 A | 5/1975 | Rooz et al. |
| 3,995,075 A | 11/1976 | Cernauskas et al. |
| 4,011,388 A | 3/1977 | Murphy et al. |
| 4,082,212 A | 4/1978 | Headrick et al. |
| 4,201,149 A | 5/1980 | Koester et al. |
| 4,226,243 A | 10/1980 | Shalaby et al. |
| 4,269,713 A | 5/1981 | Yamashita et al. |
| 4,290,383 A | 9/1981 | Pfender |
| 4,329,383 A | 5/1982 | Joh |
| 4,343,931 A | 8/1982 | Barrows |
| 4,459,252 A | 7/1984 | MacGregor |
| 4,489,670 A | 12/1984 | Mosser et al. |
| 4,529,792 A | 7/1985 | Barrows |
| 4,560,374 A | 12/1985 | Hammerslag |
| 4,611,051 A | 9/1986 | Hayes et al. |
| 4,616,593 A | 10/1986 | Kawamura et al. |
| 4,629,563 A | 12/1986 | Wrasidlo |
| 4,640,846 A | 2/1987 | Kuo |

(Continued)

FOREIGN PATENT DOCUMENTS

DE   42 24 401   1/1994

(Continued)

OTHER PUBLICATIONS

U.S. Appl. No. 09/894,293, filed Jun. 27, 2001, Roorda et al.

(Continued)

*Primary Examiner*—Laura Edwards
(74) *Attorney, Agent, or Firm*—Squire, Sanders & Dempsey L.L.P.

(57) ABSTRACT

A stent fixture for supporting a stent during formation of a coating is provided.

23 Claims, 5 Drawing Sheets

U.S. PATENT DOCUMENTS

| | | |
|---|---|---|
| 4,656,242 A | 4/1987 | Swan et al. |
| 4,733,665 A | 3/1988 | Palmaz |
| 4,762,128 A | 8/1988 | Rosenbluth |
| 4,798,585 A | 1/1989 | Inoue et al. |
| 4,800,882 A | 1/1989 | Gianturco |
| 4,822,535 A | 4/1989 | Ekman et al. |
| 4,839,055 A | 6/1989 | Ishizaki et al. |
| 4,846,791 A | 7/1989 | Hattler et al. |
| 4,865,879 A | 9/1989 | Finlay |
| 4,882,168 A | 11/1989 | Casey et al. |
| 4,886,062 A | 12/1989 | Wiktor |
| 4,893,623 A | 1/1990 | Rosenbluth |
| 4,906,423 A | 3/1990 | Frisch |
| 4,931,287 A | 6/1990 | Bae et al. |
| 4,941,870 A | 7/1990 | Okada et al. |
| 4,955,899 A | 9/1990 | Della Corna et al. |
| 4,976,736 A | 12/1990 | White et al. |
| 4,977,901 A | 12/1990 | Ofstead |
| 4,992,312 A | 2/1991 | Frisch |
| 5,017,420 A | 5/1991 | Marikar |
| 5,019,096 A | 5/1991 | Fox, Jr. et al. |
| 5,033,405 A | 7/1991 | Yamada et al. |
| 5,037,392 A | 8/1991 | Hillstead |
| 5,037,427 A | 8/1991 | Harada et al. |
| 5,059,211 A | 10/1991 | Stack et al. |
| 5,095,848 A | 3/1992 | Ikeno |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,171,445 A | 12/1992 | Zepf |
| 5,188,734 A | 2/1993 | Zepf |
| 5,201,314 A | 4/1993 | Bosley et al. |
| 5,219,980 A | 6/1993 | Swidler |
| 5,229,045 A | 7/1993 | Soldani |
| 5,234,457 A | 8/1993 | Andersen |
| 5,242,399 A | 9/1993 | Lau et al. |
| 5,258,020 A | 11/1993 | Froix |
| 5,264,246 A | 11/1993 | Ikeno |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,286 A | 4/1994 | Stack et al. |
| 5,306,501 A | 4/1994 | Viegas et al. |
| 5,306,786 A | 4/1994 | Moens et al. |
| 5,308,338 A | 5/1994 | Helfrich |
| 5,328,471 A | 7/1994 | Slepian |
| 5,330,768 A | 7/1994 | Park et al. |
| 5,342,621 A | 8/1994 | Eury |
| 5,358,740 A | 10/1994 | Bornside et al. |
| 5,370,684 A | 12/1994 | Vallana et al. |
| 5,378,511 A | 1/1995 | Cardinali et al. |
| 5,380,299 A | 1/1995 | Fearnot et al. |
| 5,417,981 A | 5/1995 | Endo et al. |
| 5,421,955 A | 6/1995 | Lau et al. |
| 5,443,496 A | 8/1995 | Schwartz et al. |
| 5,447,724 A | 9/1995 | Helmus et al. |
| 5,455,040 A | 10/1995 | Marchant |
| 5,458,683 A | 10/1995 | Taylor et al. |
| 5,462,990 A | 10/1995 | Hubbell et al. |
| 5,464,650 A | 11/1995 | Berg et al. |
| 5,485,496 A | 1/1996 | Lee et al. |
| 5,514,154 A | 5/1996 | Lau et al. |
| 5,516,560 A | 5/1996 | Harayama et al. |
| 5,516,881 A | 5/1996 | Lee et al. |
| 5,520,697 A * | 5/1996 | Lindenberg et al. ......... 606/108 |
| 5,527,337 A | 6/1996 | Stack et al. |
| 5,537,729 A | 7/1996 | Kolobow |
| 5,538,493 A | 7/1996 | Gerken et al. |
| 5,558,900 A | 9/1996 | Fan et al. |
| 5,569,295 A | 10/1996 | Lam |
| 5,569,463 A | 10/1996 | Helmus et al. |
| 5,578,048 A | 11/1996 | Pasqualucci et al. |
| 5,578,073 A | 11/1996 | Haimovich et al. |
| 5,584,877 A | 12/1996 | Miyake et al. |
| 5,603,721 A | 2/1997 | Lau et al. |
| 5,605,696 A | 2/1997 | Eury et al. |
| 5,607,442 A | 3/1997 | Fischell et al. |
| 5,607,467 A | 3/1997 | Froix |
| 5,609,629 A | 3/1997 | Fearnot et al. |
| 5,610,241 A | 3/1997 | Lee et al. |
| 5,611,775 A | 3/1997 | Machold et al. |
| 5,616,338 A | 4/1997 | Fox, Jr. et al. |
| 5,624,411 A | 4/1997 | Tuch |
| 5,628,730 A | 5/1997 | Shapland et al. |
| 5,628,786 A | 5/1997 | Banas et al. |
| 5,637,113 A | 6/1997 | Tartaglia et al. |
| 5,643,580 A | 7/1997 | Subramaniam |
| 5,644,020 A | 7/1997 | Timmermann et al. |
| 5,649,977 A | 7/1997 | Campbell |
| 5,656,082 A | 8/1997 | Takatsuki et al. |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,687,906 A | 11/1997 | Nakagawa |
| 5,700,286 A | 12/1997 | Tartaglia et al. |
| 5,702,754 A | 12/1997 | Zhong |
| 5,707,385 A | 1/1998 | Williams |
| 5,711,958 A | 1/1998 | Cohn et al. |
| 5,713,949 A | 2/1998 | Jayaraman |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,741,554 A | 4/1998 | Tisone |
| 5,746,998 A | 5/1998 | Torchilin et al. |
| 5,756,553 A | 5/1998 | Iguchi et al. |
| 5,759,205 A | 6/1998 | Valentini |
| 5,766,710 A | 6/1998 | Turnlund et al. |
| 5,769,883 A | 6/1998 | Buscemi et al. |
| 5,772,864 A | 6/1998 | Møller et al. |
| 5,776,184 A | 7/1998 | Tuch |
| 5,783,657 A | 7/1998 | Pavlin et al. |
| 5,788,626 A | 8/1998 | Thompson |
| 5,788,979 A | 8/1998 | Alt et al. |
| 5,800,392 A | 9/1998 | Racchini |
| 5,820,917 A | 10/1998 | Tuch |
| 5,823,996 A | 10/1998 | Sparks |
| 5,824,048 A | 10/1998 | Tuch |
| 5,824,049 A | 10/1998 | Ragheb et al. |
| 5,830,178 A | 11/1998 | Jones et al. |
| 5,833,659 A | 11/1998 | Kranys |
| 5,836,965 A | 11/1998 | Jendersee et al. |
| 5,837,008 A | 11/1998 | Berg et al. |
| 5,837,313 A | 11/1998 | Ding et al. |
| 5,843,172 A | 12/1998 | Yan |
| 5,849,859 A | 12/1998 | Acemoglu |
| 5,851,508 A | 12/1998 | Greff et al. |
| 5,854,376 A | 12/1998 | Higashi |
| 5,855,598 A | 1/1999 | Pinchuk |
| 5,855,600 A | 1/1999 | Alt |
| 5,855,684 A | 1/1999 | Bergmann |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,891,108 A | 4/1999 | Leone et al. |

| | | | | | | |
|---|---|---|---|---|---|---|
| 5,891,507 | A | 4/1999 | Jayaraman | 6,174,329 B1 | 1/2001 | Callol et al. |
| 5,895,407 | A | 4/1999 | Jayaraman | 6,177,523 B1 | 1/2001 | Reich et al. |
| 5,897,911 | A | 4/1999 | Loeffler | 6,180,632 B1 | 1/2001 | Myers et al. |
| 5,902,631 | A | 5/1999 | Wang et al. | 6,183,503 B1 * | 2/2001 | Hart et al. .................... 623/1.1 |
| 5,902,875 | A | 5/1999 | Roby et al. | 6,194,034 B1 | 2/2001 | Nishi et al. |
| 5,905,168 | A | 5/1999 | Dos Santos et al. | 6,197,013 B1 | 3/2001 | Reed et al. |
| 5,910,564 | A | 6/1999 | Gruning et al. | 6,203,551 B1 | 3/2001 | Wu |
| 5,911,752 | A | 6/1999 | Dustrude et al. | 6,203,569 B1 | 3/2001 | Wijay |
| 5,914,387 | A | 6/1999 | Roby et al. | 6,206,915 B1 | 3/2001 | Fagan et al. |
| 5,919,893 | A | 7/1999 | Roby et al. | 6,211,249 B1 | 4/2001 | Cohn et al. |
| 5,922,393 | A | 7/1999 | Jayaraman | 6,214,115 B1 | 4/2001 | Taylor et al. |
| 5,925,720 | A | 7/1999 | Kataoka et al. | 6,214,901 B1 | 4/2001 | Chudzik et al. |
| 5,928,279 | A | 7/1999 | Shannon et al. | 6,228,072 B1 | 5/2001 | Omaleki et al. |
| 5,932,299 | A | 8/1999 | Katoot | 6,231,600 B1 | 5/2001 | Zhong |
| 5,935,135 | A | 8/1999 | Bramfitt et al. | 6,235,340 B1 | 5/2001 | Lee et al. |
| 5,948,018 | A | 9/1999 | Dereume et al. | 6,240,616 B1 | 6/2001 | Yan |
| 5,955,509 | A | 9/1999 | Webber et al. | 6,244,575 B1 | 6/2001 | Vaartstra et al. |
| 5,958,385 | A | 9/1999 | Tondeur et al. | 6,245,099 B1 | 6/2001 | Edwin et al. |
| 5,962,138 | A | 10/1999 | Kolluri et al. | 6,245,753 B1 | 6/2001 | Byun et al. |
| 5,968,091 | A | 10/1999 | Pinchuk et al. | 6,245,760 B1 | 6/2001 | He et al. |
| 5,971,954 | A | 10/1999 | Conway et al. | 6,248,129 B1 | 6/2001 | Froix |
| 5,972,027 | A | 10/1999 | Johnson | 6,248,398 B1 | 6/2001 | Talieh et al. |
| 5,980,928 | A | 11/1999 | Terry | 6,251,136 B1 | 6/2001 | Guruwaiya et al. |
| 5,980,972 | A | 11/1999 | Ding | 6,254,632 B1 | 7/2001 | Wu et al. |
| 5,984,449 | A | 11/1999 | Tajika et al. | 6,258,121 B1 | 7/2001 | Yang et al. |
| 5,997,517 | A | 12/1999 | Whitbourne | 6,258,371 B1 | 7/2001 | Koulik et al. |
| 6,010,530 | A | 1/2000 | Goicoechea | 6,261,320 B1 | 7/2001 | Tam et al. |
| 6,010,573 | A | 1/2000 | Bowlin | 6,262,034 B1 | 7/2001 | Mathiowitz et al. |
| 6,011,125 | A | 1/2000 | Lohmeijer et al. | 6,270,504 B1 | 8/2001 | Lorentzen Cornelius et al. |
| 6,013,099 | A | 1/2000 | Dinh et al. | 6,270,788 B1 | 8/2001 | Koulik et al. |
| 6,015,541 | A | 1/2000 | Greff et al. | 6,273,878 B1 | 8/2001 | Muni |
| 6,030,371 | A | 2/2000 | Pursley | 6,273,908 B1 | 8/2001 | Ndondo-Lay |
| 6,033,582 | A | 3/2000 | Lee et al. | 6,273,910 B1 | 8/2001 | Limon |
| 6,034,204 | A | 3/2000 | Mohr et al. | 6,273,913 B1 | 8/2001 | Wright et al. |
| 6,042,875 | A | 3/2000 | Ding et al. | 6,277,449 B1 | 8/2001 | Kolluri et al. |
| 6,045,899 | A | 4/2000 | Wang et al. | 6,279,368 B1 | 8/2001 | Escano et al. |
| 6,051,576 | A | 4/2000 | Ashton et al. | 6,283,947 B1 | 9/2001 | Mirzaee |
| 6,051,648 | A | 4/2000 | Rhee et al. | 6,283,949 B1 | 9/2001 | Roorda |
| 6,054,553 | A | 4/2000 | Groth et al. | 6,284,305 B1 | 9/2001 | Ding et al. |
| 6,056,993 | A | 5/2000 | Leidner et al. | 6,287,249 B1 | 9/2001 | Tam et al. |
| 6,059,714 | A | 5/2000 | Armini et al. | 6,287,628 B1 | 9/2001 | Hossainy et al. |
| 6,060,451 | A | 5/2000 | DiMaio et al. | 6,299,604 B1 | 10/2001 | Ragheb et al. |
| 6,060,518 | A | 5/2000 | Kabanov et al. | 6,306,165 B1 | 10/2001 | Patnaik et al. |
| 6,068,202 | A | 5/2000 | Hynes et al. | 6,306,176 B1 | 10/2001 | Whitbourne |
| 6,071,305 | A | 6/2000 | Brown et al. | 6,322,847 B1 | 11/2001 | Zhong et al. |
| 6,080,488 | A | 6/2000 | Hostettler et al. | 6,331,191 B1 | 12/2001 | Chobotov |
| 6,096,070 | A | 8/2000 | Ragheb et al. | 6,331,313 B1 | 12/2001 | Wong et al. |
| 6,099,562 | A | 8/2000 | Ding et al. | 4,733,665 C2 | 1/2002 | Palmaz |
| 6,106,889 | A | 8/2000 | Jayaraman | 6,335,029 B1 | 1/2002 | Kamath et al. |
| 6,110,188 | A | 8/2000 | Narciso, Jr. | 6,344,035 B1 | 2/2002 | Chudzik et al. |
| 6,110,483 | A | 8/2000 | Whitbourne et al. | 6,346,110 B2 | 2/2002 | Wu |
| 6,113,629 | A | 9/2000 | Ken | 6,358,556 B1 | 3/2002 | Ding et al. |
| 6,120,491 | A | 9/2000 | Kohn et al. | 6,358,567 B2 | 3/2002 | Pham et al. |
| 6,120,536 | A | 9/2000 | Ding et al. | 6,364,903 B2 | 4/2002 | Tseng et al. |
| 6,120,788 | A | 9/2000 | Barrows | 6,368,658 B1 | 4/2002 | Schwarz et al. |
| 6,120,847 | A | 9/2000 | Yang et al. | 6,372,283 B1 | 4/2002 | Shim et al. |
| 6,120,904 | A | 9/2000 | Hostettler et al. | 6,379,381 B1 | 4/2002 | Hossainy et al. |
| 6,121,027 | A | 9/2000 | Clapper et al. | 6,383,215 B1 | 5/2002 | Sass |
| 6,126,686 | A | 10/2000 | Badylak et al. | 6,387,118 B1 | 5/2002 | Hanson |
| 6,129,755 | A | 10/2000 | Mathis et al. | 6,387,379 B1 | 5/2002 | Goldberg et al. |
| 6,129,761 | A | 10/2000 | Hubbell | 6,395,326 B1 | 5/2002 | Castro et al. |
| 6,136,333 | A | 10/2000 | Cohn et al. | 6,407,009 B1 | 6/2002 | You et al. |
| 6,140,127 | A | 10/2000 | Sprague | 6,416,543 B1 | 7/2002 | Hilaire et al. |
| 6,140,431 | A | 10/2000 | Kinker et al. | 6,419,692 B1 | 7/2002 | Yang et al. |
| 6,143,354 | A | 11/2000 | Koulik et al. | 6,435,798 B1 | 8/2002 | Satoh |
| 6,143,370 | A | 11/2000 | Panagiotou et al. | 6,440,221 B2 | 8/2002 | Shamouilian et al. |
| 6,153,252 | A | 11/2000 | Hossainy et al. | 6,451,373 B1 | 9/2002 | Hossainy et al. |
| 6,156,373 | A | 12/2000 | Zhong et al. | 6,475,779 B2 | 11/2002 | Mathiowitz et al. |
| 6,159,978 | A | 12/2000 | Myers et al. | 6,482,834 B2 | 11/2002 | Spada et al. |
| 6,165,212 | A | 12/2000 | Dereume et al. | 6,494,862 B1 | 12/2002 | Ray et al. |
| 6,165,267 | A | 12/2000 | Torczynski | 6,503,538 B1 | 1/2003 | Chu et al. |
| 6,171,334 | B1 | 1/2001 | Cox | 6,503,556 B2 | 1/2003 | Harish et al. |
| 6,172,167 | B1 | 1/2001 | Stapert et al. | 6,503,954 B1 | 1/2003 | Bhat et al. |

| | | | | | | |
|---|---|---|---|---|---|---|
| 6,506,437 B1 | 1/2003 | Harish et al. | | 6,955,723 B2 | 10/2005 | Pacetti et al. |
| 6,517,534 B1 | 2/2003 | McGovern et al. | | 7,169,172 B2 * | 1/2007 | Levine et al. ............... 623/1.11 |
| 6,517,889 B1 | 2/2003 | Jayaraman | | 2001/0007083 A1 | 7/2001 | Roorda |
| 6,521,284 B1 | 2/2003 | Parsons et al. | | 2001/0029351 A1 | 10/2001 | Falotico et al. |
| 6,524,347 B1 | 2/2003 | Myers et al. | | 2001/0037145 A1 | 11/2001 | Guruwaiya et al. |
| 6,527,801 B1 | 3/2003 | Dutta | | 2002/0005206 A1 | 1/2002 | Falotico et al. |
| 6,527,863 B1 | 3/2003 | Pacetti et al. | | 2002/0007213 A1 | 1/2002 | Falotico et al. |
| 6,528,526 B1 | 3/2003 | Myers et al. | | 2002/0007214 A1 | 1/2002 | Falotico |
| 6,530,950 B1 | 3/2003 | Alvarado et al. | | 2002/0007215 A1 | 1/2002 | Falotico et al. |
| 6,530,951 B1 | 3/2003 | Bates et al. | | 2002/0050220 A1 | 5/2002 | Schueller et al. |
| 6,534,112 B1 | 3/2003 | Bouchier et al. | | 2002/0051730 A1 | 5/2002 | Bodnar et al. |
| 6,540,776 B2 | 4/2003 | Sanders Millare et al. | | 2002/0077693 A1 | 6/2002 | Barclay et al. |
| 6,544,223 B1 | 4/2003 | Kokish | | 2002/0082679 A1 | 6/2002 | Sirhan et al. |
| 6,544,543 B1 | 4/2003 | Mandrusov et al. | | 2002/0087123 A1 | 7/2002 | Hossainy et al. |
| 6,544,582 B1 | 4/2003 | Yoe | | 2002/0091433 A1 | 7/2002 | Ding et al. |
| 6,555,157 B1 | 4/2003 | Hossainy | | 2002/0111590 A1 | 8/2002 | Davila et al. |
| 6,558,733 B1 | 5/2003 | Hossainy et al. | | 2002/0165608 A1 | 11/2002 | Llanos et al. |
| 6,562,136 B1 | 5/2003 | Chappa et al. | | 2002/0176849 A1 | 11/2002 | Slepian |
| 6,565,659 B1 | 5/2003 | Pacetti et al. | | 2002/0183581 A1 | 12/2002 | Yoe et al. |
| 6,572,644 B1 | 6/2003 | Moein | | 2002/0188037 A1 | 12/2002 | Chudzik et al. |
| 6,572,651 B1 | 6/2003 | De Scheerder et al. | | 2002/0188277 A1 | 12/2002 | Roorda et al. |
| 6,575,933 B1 | 6/2003 | Wittenberger et al. | | 2003/0004141 A1 | 1/2003 | Brown |
| 6,585,755 B2 | 7/2003 | Jackson et al. | | 2003/0028243 A1 | 2/2003 | Bates et al. |
| 6,585,765 B1 | 7/2003 | Hossainy et al. | | 2003/0028244 A1 | 2/2003 | Bates et al. |
| 6,585,926 B1 | 7/2003 | Mirzaee | | 2003/0031780 A1 | 2/2003 | Chudzik et al. |
| 6,605,154 B1 | 8/2003 | Villareal | | 2003/0032767 A1 | 2/2003 | Tada et al. |
| 6,610,087 B1 | 8/2003 | Zarbatany et al. | | 2003/0036794 A1 | 2/2003 | Ragheb et al. |
| 6,613,432 B2 | 9/2003 | Zamora et al. | | 2003/0039689 A1 | 2/2003 | Chen et al. |
| 6,616,765 B1 | 9/2003 | Hossaony et al. | | 2003/0040712 A1 | 2/2003 | Ray et al. |
| 6,620,617 B2 | 9/2003 | Mathiowitz et al. | | 2003/0040790 A1 | 2/2003 | Furst |
| 6,623,448 B2 | 9/2003 | Slater | | 2003/0059520 A1 | 3/2003 | Chen et al. |
| 6,625,486 B2 | 9/2003 | Lundkvist et al. | | 2003/0060877 A1 | 3/2003 | Falotico et al. |
| 6,641,611 B2 | 11/2003 | Jayaraman | | 2003/0065377 A1 | 4/2003 | Davila et al. |
| 6,645,135 B1 | 11/2003 | Bhat | | 2003/0072868 A1 | 4/2003 | Harish et al. |
| 6,645,195 B1 | 11/2003 | Bhat et al. | | 2003/0073961 A1 | 4/2003 | Happ |
| 6,656,216 B1 | 12/2003 | Hossainy et al. | | 2003/0083646 A1 | 5/2003 | Sirhan et al. |
| 6,656,506 B1 | 12/2003 | Wu et al. | | 2003/0083739 A1 | 5/2003 | Cafferata |
| 6,660,034 B1 | 12/2003 | Mandrusov et al. | | 2003/0088307 A1 | 5/2003 | Shulze et al. |
| 6,663,662 B2 | 12/2003 | Pacetti et al. | | 2003/0097088 A1 | 5/2003 | Pacetti |
| 6,663,880 B1 | 12/2003 | Roorda et al. | | 2003/0097173 A1 | 5/2003 | Dutta |
| 6,666,880 B1 | 12/2003 | Chiu et al. | | 2003/0105518 A1 | 6/2003 | Dutta |
| 6,673,154 B1 | 1/2004 | Pacetti et al. | | 2003/0113439 A1 | 6/2003 | Pacetti et al. |
| 6,673,385 B1 | 1/2004 | Ding et al. | | 2003/0150380 A1 | 8/2003 | Yoe |
| 6,676,700 B1 | 1/2004 | Jacobs et al. | | 2003/0158517 A1 | 8/2003 | Kokish |
| 6,682,771 B2 | 1/2004 | Zhong et al. | | 2003/0190406 A1 | 10/2003 | Hossainy et al. |
| 6,689,099 B2 | 2/2004 | Mirzaee | | 2003/0211230 A1 | 11/2003 | Pacetti et al. |
| 6,689,350 B2 | 2/2004 | Uhrich | | 2003/0215564 A1 | 11/2003 | Heller et al. |
| 6,695,920 B1 | 2/2004 | Pacetti et al. | | 2004/0018296 A1 | 1/2004 | Castro et al. |
| 6,706,013 B1 | 3/2004 | Bhat et al. | | 2004/0029952 A1 | 2/2004 | Chen et al. |
| 6,709,514 B1 | 3/2004 | Hossainy | | 2004/0047978 A1 | 3/2004 | Hossainy et al. |
| 6,712,845 B2 | 3/2004 | Hossainy | | 2004/0047980 A1 | 3/2004 | Pacetti et al. |
| 6,713,119 B2 | 3/2004 | Hossainy et al. | | 2004/0052858 A1 | 3/2004 | Wu et al. |
| 6,716,444 B1 | 4/2004 | Castro et al. | | 2004/0052859 A1 | 3/2004 | Wu et al. |
| 6,723,120 B2 | 4/2004 | Yan | | 2004/0054104 A1 | 3/2004 | Pacetti |
| 6,723,373 B1 | 4/2004 | Narayanan et al. | | 2004/0060508 A1 | 4/2004 | Pacetti et al. |
| 6,730,064 B2 | 5/2004 | Ragheb et al. | | 2004/0062853 A1 | 4/2004 | Pacetti et al. |
| 6,733,768 B2 | 5/2004 | Hossainy et al. | | 2004/0063805 A1 | 4/2004 | Pacetti et al. |
| 6,740,040 B1 | 5/2004 | Mandrusov et al. | | 2004/0071861 A1 | 4/2004 | Mandrusov et al. |
| 6,743,462 B1 | 6/2004 | Pacetti | | 2004/0072922 A1 | 4/2004 | Hossainy et al. |
| 6,746,773 B2 | 6/2004 | Llanos et al. | | 2004/0073298 A1 | 4/2004 | Hossainy |
| 6,749,626 B1 | 6/2004 | Bhat et al. | | 2004/0086542 A1 | 5/2004 | Hossainy et al. |
| 6,753,071 B1 | 6/2004 | Pacetti | | 2004/0086550 A1 | 5/2004 | Roorda et al. |
| 6,758,859 B1 | 7/2004 | Dang et al. | | 2004/0096504 A1 | 5/2004 | Michal |
| 6,759,054 B2 | 7/2004 | Chen et al. | | 2004/0098117 A1 | 5/2004 | Hossainy et al. |
| 6,764,505 B1 | 7/2004 | Hossainy et al. | | 2004/0172804 A1 * | 9/2004 | Hopkins ..................... 29/558 |
| 6,776,796 B2 | 8/2004 | Falotico et al. | | 2004/0191405 A1 | 9/2004 | Kerrigan |
| 6,780,424 B2 | 8/2004 | Claude | | 2004/0194704 A1 * | 10/2004 | Chappa et al. ............... 118/719 |
| 6,790,228 B2 | 9/2004 | Hossainy et al. | | 2004/0213893 A1 | 10/2004 | Boulais |
| 6,818,063 B1 | 11/2004 | Kerrigan | | 2005/0069630 A1 | 3/2005 | Fox et al. |
| 6,824,559 B2 | 11/2004 | Michal | | | | |
| 6,860,946 B2 | 3/2005 | Hossainy et al. | | | | |
| 6,887,510 B2 | 5/2005 | Villareal | | | | |
| 6,890,583 B2 | 5/2005 | Chudzik et al. | | | | |

| | | |
|---|---|---|
| 2005/0074544 A1 | 4/2005 | Pacetti et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 627 226 | 12/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 875 218 | 11/1998 |
| EP | 0 879 595 | 11/1998 |
| EP | 0 897 701 | 2/1999 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 05009726 A | 1/1993 |
| JP | 11299901 | 11/1999 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 90/01969 | 3/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/16386 | 4/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/00112 | 1/2001 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/008995 | 1/2004 |
| WO | WO 2004/009145 | 1/2004 |

OTHER PUBLICATIONS

U.S. Appl. No. 09/997,390, filed Nov. 30, 2001, Pacetti.
U.S. Appl. No. 10/040,538, filed Dec. 28, 2001, Pacetti et al.
U.S. Appl. No. 10/255,913, filed Sep. 26, 2002, Tang et al.
U.S. Appl. No. 10/262,161, filed Sep. 30, 2002, Pacetti
U.S. Appl. No. 10/266,479, filed Oct. 8, 2002, Hossainy.
U.S. Appl. No. 10/304,669, filed Nov. 25, 2002, Madriaga et al.
U.S. Appl. No. 10/319,042, filed Dec. 12, 2002, Van Sciver et al.
U.S. Appl. No. 10/330,412, filed Dec. 27, 2002, Hossainy et al.
U.S. Appl. No. 10/376,027, filed Feb. 26, 2003, Kokish et al.
U.S. Appl. No. 10/438,378, filed May 15, 2003, Esbeck et al.
U.S. Appl. No. 10/660,853, filed Sep. 12, 2003, Pacetti et al.
U.S. Appl. No. 10/729,551, filed Dec. 5, 2003, Pacetti.
U.S. Appl. No. 10/729,728, filed Dec. 5, 2003, Pacetti.
U.S. Appl. No. 10/750,312, filed Dec. 30, 2003, Desnoyer et al.
U.S. Appl. No. 10/805,047, filed Mar. 18, 2004, Yip et al.
U.S. Appl. No. 10/813,845, filed Mar. 30, 2004, Pacetti.
U.S. Appl. No. 10/817,642, filed Apr. 2, 2004, Kerrigan.
Anonymous, *Cardiologists Draw—Up The Dream Stent*, Clinica 710:15 (Jun. 17, 1996), http://www..dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Coating Techniques, *Air Knife Coating*, http://www.ferron-magnetic.co.uk/coatings/airknife.htm, 1 page, printed Jul. 1, 2003.
Coating Techniques, *Gap Coating*, http://www.ferron-magnetic.co.uk/coatings/knife.htm, 1 page, printed Jul. 1, 2003.
Coating Techniques, *Gravure Coating*, http://www.ferron-magnetic.co.uk/coatings/gravure.htm, 2 pages, printed Jul. 1, 2003.
Coating Techniques, *Reverse Roll Coating*, http://www.ferron-magnetic.co.uk/coatings/revroll.htm, 2 pages, printed Jul. 1, 2003.
Dev et al, *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Forrester et al., *A Paradigm for Restenosis Based on Cell Biology: Clues for the Development of New Preventive Therapies*; J. Am. Coll. Cardio. 1991; 17:758-769.

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Illbruck Sealant Systems, *Application: Window and Perimeter Silicone*, http://www.willseal.com/usa/produktuebersicht/dichtstoffe/perwindow/verlege_anleitunq . . . ., printed Nov. 29, 2004 (3 pages).

Inoue et al., *An AB block copolymer of oligo(methyl methacrylate) and poly(acrylic acid) for micellar delivery of hydrophobic drugs*, Journal of Controlled Release 51:221-229 (1998).

*International Search Report and Written Opinion*, dated Mar. 1, 2005 for PCT Application No. PCT/US2004/031185, filed Sep. 22, 2004 (14 pages).

Kataoka et al., *Block copolymer micelles as vehicles for drug delivery*, Journal of Controlled Release 24:119-132 (1993).

Kim, *Solid State Sintering*, AMSE 604 Solid State Reactions and Sintering, Electroceramic laboratory in Dept. of Materials Science & Engineering, POSTECH, Pohang University of Science and Technology (20 pages).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan*, Novel Endothelin Receptor; Chemical Abstract 125:212307 (1996).

van Beusekom et al., *Coronary stent coatings*, Coronary Artery Disease 5(7):590-596 (Jul. 1994).

Van Iseghem, *Important Concepts on Coating Plastics From a Formulator's Perspective*, Modern Paint and Coatings, pp. 30-38 (Feb. 1998).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Search Report for PCT/US2006/023636 filed Jun. 16, 2006, mailed Nov. 9, 2006, 11 pgs.

\* cited by examiner

STENT FIXTURE AND METHOD FOR REDUCING COATING DEFECTS

TECHNICAL FIELD

This invention relates generally to stent fixtures, and more particularly, but not exclusively, provides a stent fixture and method for reducing coating defects on stents.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giant-urco, and U.S. Pat. No. 4,886,062 issued to Wiktor.

Figure 1:
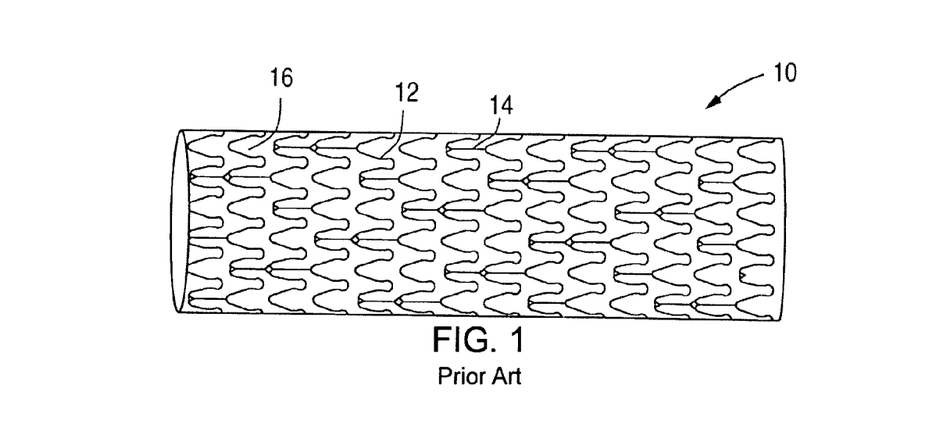
FIG. 1 is a diagram illustrating a conventional stent.

FIG. 1 illustrates a conventional stent 10 formed from a plurality of struts 12. The plurality of struts 12 are radially expandable and interconnected by connecting elements 14 that are disposed between the adjacent struts 12, leaving lateral openings or gaps 16 between the adjacent struts 12. The struts 12 and the connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Accordingly, a new stent fixture and method of use are needed to minimize coating defects.

SUMMARY

In accordance with one embodiment a stent fixture for supporting a stent during formation of a coating is provided comprising a structure having arm elements extending from the structure. The arm elements can be are configured to allow an inner side of a stent to rest on and be supported by the arm elements. The structure can support one end of the stent such that the fixture can, in some embodiments, additionally comprise a second structure for support an opposing end of the stent. The second structure can comprise arm elements extending out from the second structure. The arm elements of the second structure are configured to allow the inner side of the stent to rest on and be supported by the arm elements of the second structure. In some embodiments, the fixture can include a third structure connecting the structure to the second structure and extending through a longitudinal bore of the stent. The stent can be securely pinched between the plurality of arm elements of the structures.

In accordance with another aspect of the invention, methods of coating a stent using the above-described fixtures are provided.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 2:
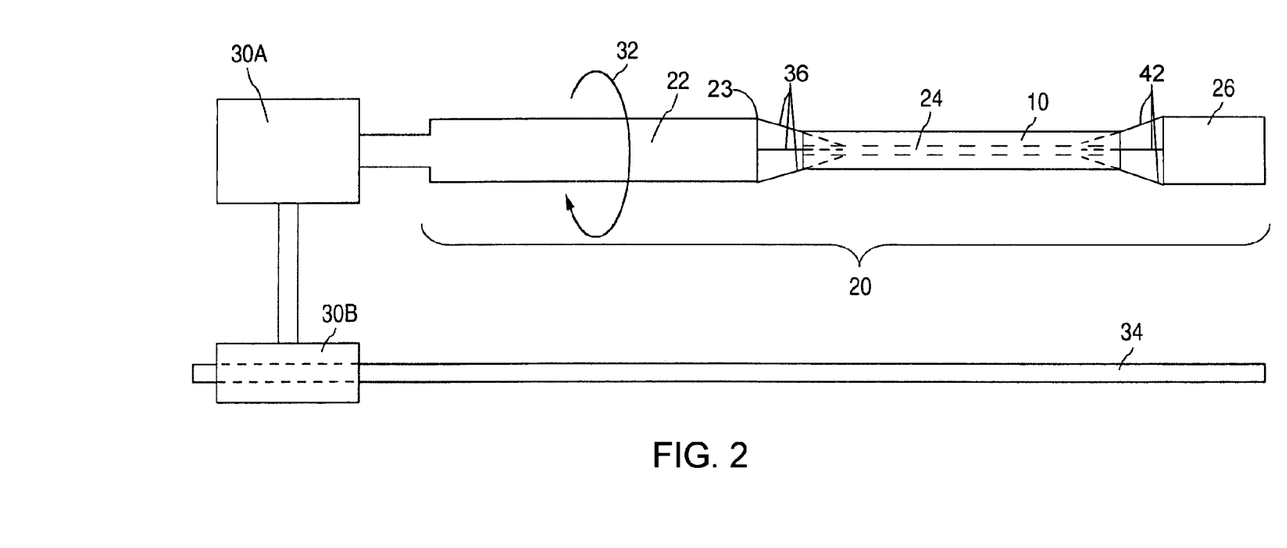
FIG. 2 is a diagram illustrating a stent fixture in accordance with an embodiment of the invention.

FIG. 2 illustrates a stent mandrel fixture 20 in accordance with an embodiment of the invention. The fixture 20 for supporting the stent 10 is illustrated to include a support member 22, a mandrel 24, and a lock member 26. The support member 22 can connect to a motor 30A so as to provide rotational motion about the longitudinal axis of the stent 10, as depicted by arrow 32, during a coating process. Another motor 30B can also be provided for moving the support member 22 in a linear direction, back and forth, along a rail 34.

Figure 3:
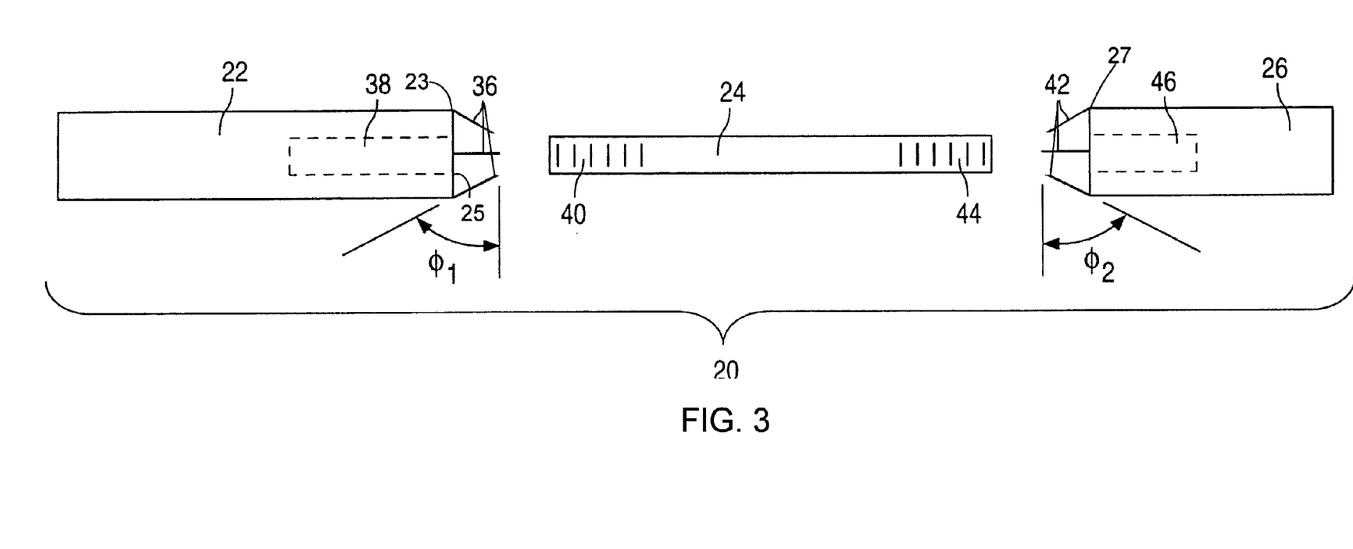
FIG. 3 is a diagram illustrating a disassembled view of stent fixture of FIG. 2.
Figure 5:
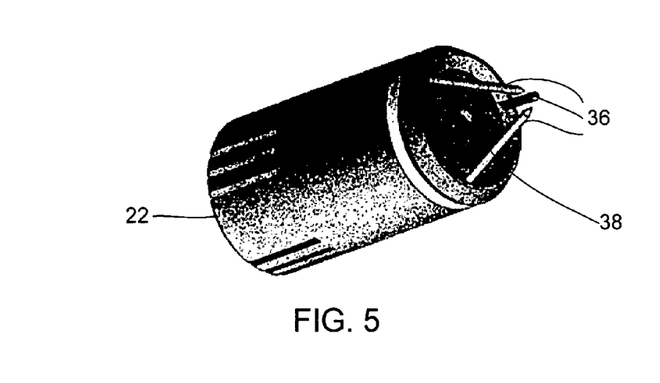
FIG. 5 is a diagram illustrating a perspective view of the support member.

FIG. 3 illustrates a disassembled view of the stent mandrel fixture 20. The support member 22, can have a generally cylindrical body and an end wall 23 which faces an end of a stent. In some embodiments, as best illustrated by FIG. 5, the end wall 23 can include a recess 25 defining an edge rim or lip protruding around the circumference of the end wall 23. A plurality of elements, support arms or wires 36 extend out from the perimeter of the support member 22, more particularly from the end wall 23. In some embodiments, the elements 36 extend out from the edge rim. The elements 36 can be, in some embodiments, tapering inwardly at an angle $\phi_1$ of about 15° to about 75°, more narrowly from about 30° to about 60°. By way of example, angle $\phi_1$ can be about 45°. If the elements are extending from edge rim of the end wall 23, an inner side of the edge rim can be slanted to accommodate for this tilt. The elements 36 can converge inwardly from an edge of the end wall 23 of the support member towards the center of the end wall 23. As is best illustrated by the figures, the elements 36 do not contact one another and allow for a sufficient entry space for the mandrel 24 to extend out from the support member 22. In other words, the spacing between the end tips of the elements 36 should be at least as wide as the diameter of the mandrel 24 used. In some embodiments, the end tip of the elements 36 can contact the mandrel 24. In other embodiments, the end tips of the elements 36 converge but yet remain spaced from the mandrel 24. The elements 36 can extend at least partially over the mandrel 24 and can prevent a stent from making contact with the mandrel. The elements 36 can also prevent the support member 22 from making contact with an end ring of the stent. The elements, wires or support arms 36 can be rigidly coupled to the support member 22 so as not be capable of pivoting about a juncture, bending or flexing when a stent is positioned thereon and/or during a coating process. Alternatively, elements 36 can have at least a partial "give" in the form of bending, flexing or pivoting. In some embodiments, at least one of the elements can be rigid while at least one is flexible, bendable or pivotable. FIG. 3 illustrates 3 elements, wires or support arms 36. In some embodiments, the numbers can be 2, 3, 5, 6, 7 or 8. Although more than 8 can be used, it may provide for excessive contact points leading to coating defects while on the other hand the amount of support is not necessarily better.

In accordance with one embodiment of the invention, the mandrel 24 can be permanently affixed to the support member 22. Alternatively, the support member 22 can include a bore 38 for receiving a first end 40 of the mandrel 24. The first end 40 of the mandrel 24 can be threaded to screw into the bore 38 or, alternatively, can be retained within the bore 38 by a friction fit. The bore 38 should be deep enough so as to allow the mandrel 24 to securely mate with the support member 22. The depth of the bore 38 can also be over-extended so as to allow a significant length of the mandrel 24 to penetrate or screw into the bore 38. The bore 38 can also extend completely through the support member 22. This would allow the length of the mandrel 24 to be adjusted to accommodate stents of various sizes.

The outer diameter of the mandrel 24 can be smaller than the inner diameter of the stent 10, as positioned on the fixture, such that the elements 36 prevent the outer surface of the mandrel 24 from making contact with the inner surface of the stent 10. A sufficient clearance between the outer surface of the mandrel 24 and the inner surface of the stent 10 should be provided to prevent the mandrel 24 from obstructing the pattern of the stent body during the coating process. By way of example, the outer diameter of the mandrel 24 can be from about 0.010 inches to about 0.040 inches when the stent 10 has an inner diameter of between about 0.025 inches and about 0.065 inches, e.g., for a coronary stent. For a peripheral stent having a larger diameter, the mandrel 24 can have larger diameters.

In some embodiments, the lock member 26 can be identical or generally similar to the support member 22. In some embodiments, the lock member 26 includes a plurality of elements, support arms or wires 42 extending out from an end wall 27 of the cylindrical body of the lock member 26. As with the elements 36 of the support member 22, elements 42 of the lock member 26 can be rigid, flexible, bendable, pivotable or any combination. In some embodiments, elements 36 can be more or less flexible, bendable or pivotably than the elements 42 of the lock member 26. Preferably, the degree of fexiblity or rigidness is the same. In some embodiments, elements 42 can have an inwardly tapered angle $\phi_2$. Angle $\phi_2$ can be the same as or different than the above-described angle $\phi_1$. Although 3 elements 42 have been illustrated, any suitable number such as 2, 4, 5, 6, 7, and 8 can be used. More than 8 can be used but may increase the contact areas between a stent and elements 42. A second end 44 of the mandrel 24 can be permanently affixed to the lock member 26 if the end 40 is disengagable from the support member 22. Alternatively, in accordance with another embodiment, the mandrel 24 can have a threaded second end 44 for screwing into a bore 46 of the lock member 26. The bore 46 can be of any suitable depth that would allow the lock member 26 to be incrementally moved closer to the support member 22. The bore 46 can also extend completely through the lock member 26. Accordingly, the stents 10 of any length can be securely pinched between the support and the lock members 22 and 26. In accordance with yet another embodiment, a non-threaded second end 44 and the bore 46 combination is employed such that the second end 44 can be press-fitted or friction-fitted within the bore 46 to prevent movement of the stent 10 on the stent mandrel fixture 20.

Figure 6:
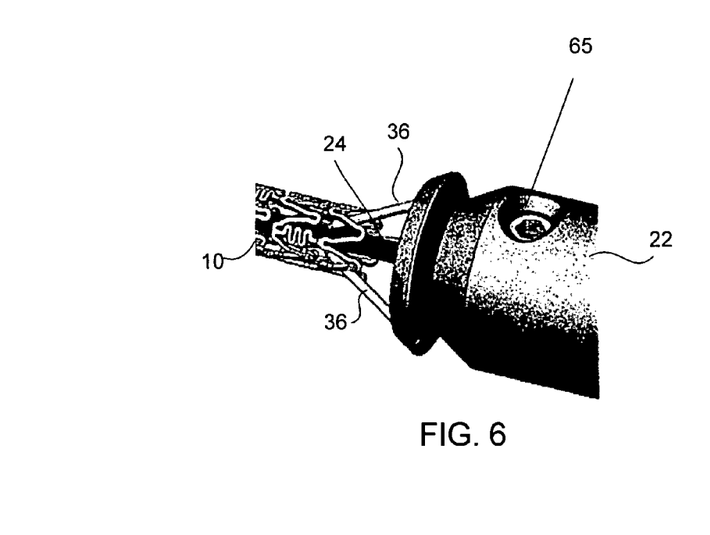
FIG. 6 is a diagram illustrating a stent mounted on the support member.

During a spray coating process, the stent 10 rests on and/or is supported by the elements, support arms or wires 36 and 42, as will be discussed in further detail in conjunction with FIG. 6 and FIG. 9 below. In an embodiment of the invention, the elements, support arms or wires 36 and 42 may have diameters of about 0.004 inches to about 0.006 inches. In some embodiments, the diameter of the wires is of sufficient size so as to allow for the wires to be fittingly placed in a crown of the end rings of a stent, as is best illustrated by FIG. 6. For example, an end ring of a stent can have a "V" shape, a "U" shape, a unique configuration to the struts. The elements 36 and 42 can be of small enough diameter so as to be placed at least partially in between the strut bodies or the space between two segments of the struts. As such, the stent 10 is only in contact with the elements, support arms or wires 36 and 42 and therefore provides minimal contact area for the collection of excess coating, thereby minimizing the formation of clumps, which can lead to further defects, such as tears and rough surfaces, when the stent 10 is removed from the fixture 20.

In order to further reduce coating defects, the elements, support arms or wires 36 and 42 may be coated with or made of, via injection molding, one or more polymeric materials having less adhesive force with the coating substance than with the elements, support arms or wires 36 and 42. Examples of a suitable polymeric materials include poly (tetrafluoroethylene) (e.g., TEFLON), fluorinated ethylene propylene ("FEP"), poly (vinylidene fluoride) ("PVDF"), poly (paraxylene), polyolefins (e.g., high density poly (ethylene) and poly (propylene)), and ME92 coating from ME92 Operations, Inc. of Providence, R.I. In an alternative embodiment of the invention, the elements, support arms or wires 36 and 42 may be made of one or more of the non-stick polymeric materials.

The components of the coating substance or composition can include a solvent or a solvent system comprising multiple solvents, a polymer or a combination of polymers, a therapeutic substance or a drug or a combination of drugs. In some embodiments, the coating substance can be exclusively a polymer or a combination of polymers (e.g., for application of a primer layer or topcoat layer). In some embodiments, the coating substance can be a drug that is polymer free. Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Representative examples of polymers that may be especially well suited for use include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can include any substance capable of exerting a therapeutic or prophylactic effect. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl(4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

Figure 4:
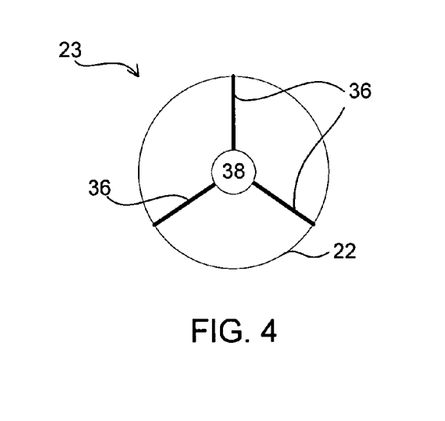
FIG. 4 is a diagram illustrating a front view of a support member of the stent fixture of FIG. 2.

FIG. 4 is a diagram illustrating a front view of the end wall 23 of the support member 22 (which can be similar to the end wall 27 of the lock member 26) of the stent mandrel fixture 20 (FIG. 2). The plurality of elements, support arms or wires 36 includes 3 wires spaced 120° apart from each other. The plurality of wires 36 extend from the circumference of the support member 22 to the bore 38. In other embodiments, the plurality of wires 36 can be spaced apart differently and/or comprise a different number of wires 36.

FIG. 5 is a diagram illustrating a perspective view of the support member 22 (which can be similar to that of the lock member 26). In an embodiment of the invention, the plurality of wires 36 may have pointed ends such that the sections of the ends facing the mandrel 24 run parallel with the mandrel 24, which enables a smoother fit between the mandrel 24 and the wires 36.

FIG. 6 is a diagram illustrating the stent 10 mounted on the stent mandrel fixture 20. When the stent 10 is mounted, the elements, support arms or wires 36 and 42 contact the mandrel and the stent 10 is supported by the wires 36 as well as the wires 42. As such, the stent 10 only interfaces with the stent mandrel fixture 20 at six minute points, thereby limiting the area at which clumps can form. Further, the support member 22 can include a lock pin 65 that extends from a surface of the member 22 through to the mandrel 24 for locking the mandrel in place.

Figure 7:
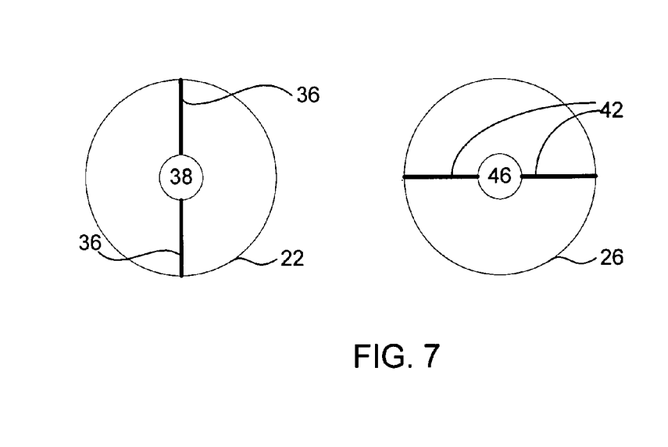
FIG. 7 is a diagram illustrating a support member and locking member according to another embodiment of the invention.

FIG. 7 is a diagram illustrating a support member 22 and a locking member 26 according to another embodiment of the invention. The support member 22 and the locking member 26 each have two wires extending there from. When the stent 10 is mounted to the members 22 and 26, one of the members is rotated 90° with respect to the other to ensure that the stent 10 is adequately supported, as is shown.

Figure 8:
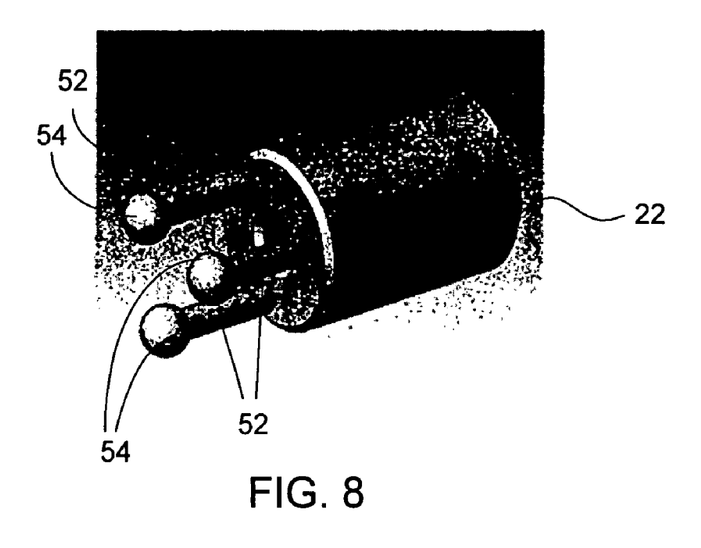
FIG. 8 is a diagram illustrating a support member according to another embodiment of the invention.
Figure 9:
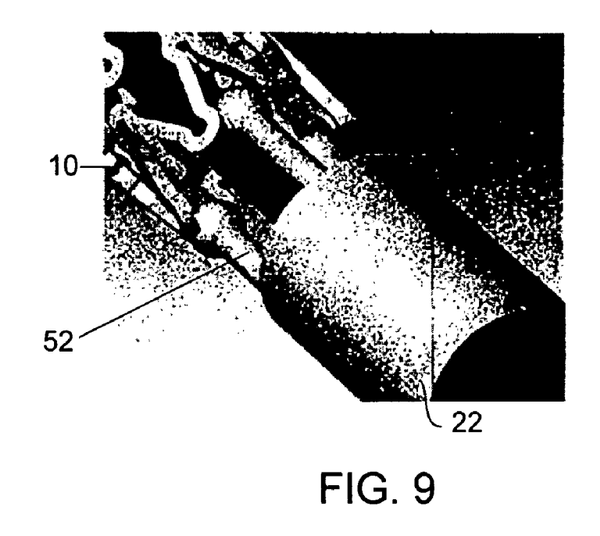
FIG. 9 is a diagram illustrating a stent mounted to the support member of FIG. 8.

FIG. 8 and FIG. 9 are diagrams illustrating a support member 22 according to another embodiment of the invention. The support member 22 of FIG. 8 and FIG. 9 has a plurality of elements, support arms or wires (e.g., 3) 52 extending laterally from the support member 22. The elements can extend parallel to the longitudinal axis of a stent or parallel to the longitudinal axis of the mandrel 24. The elements, support arms or wires 52 may be about 4 to about 8 mm in length and about 0.004 to about 0.008 inches in diameter. The elements, support arms or wires 52 each have a sphere 54 at their respective ends. In some embodiment, the spheres 54 are large enough so as to prevent the inner side of a stent from making contact with the element 52. In one embodiment, the size of the spheres 54 should be larger than a gap between the struts under which the spheres are placed and small enough so that no portion of the spheres 52 protrudes out of the outer surface of the stent. In some embodiments, a portion of the spheres can protrude out from the outer surface of the stent. By way of example, the spheres 54 can each have a diameter of about 0.015 to about 0.020 of an inch. The spheres 54 provide more rigid support than the wires 36 or 42 but provide more contact surface for a coating composition to pool, thereby slightly increasing the possibility of coating defects but still providing less surface area than conventional stent mounting fixtures.

In some embodiments, elements 36, 42 and/or 52 can extend starting from an inner position of the end wall of the support member 22 or lock member 26 to the edge of the end wall. In essence, this would be the opposite of the embodiment illustrated by FIG. 3. In this embodiment, the elements would be extending or branching outward, away from one another. The use of the mandrel 24 in this embodiment, as well as the other embodiments described above, can certainly be optional, although preferred as a second motor may be required to be coupled to the lock member 26.

Figure 10:
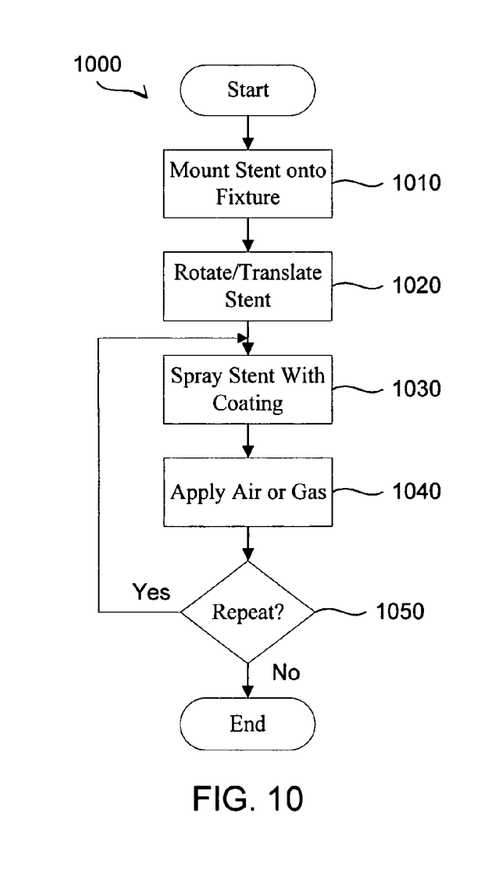
FIG. 10 is a flowchart illustrating a method of coating a stent.

FIG. 10 is a flowchart illustrating a method 1000 of coating a stent. First a stent 10 is mounted (1010) on the stent mandrel fixture 20. Mounting (1010) can include rotating the support member 22 vertically, inserting the mandrel 24 into the bore 38, mounting the stent 10 on the wires 36 or 52, and repeating for the lock member 26. A high magnification video device can also be used during the mounting (1010) to assist in adjusting the contact position between the wires 36 or 52 and the stent 10. The stent 10 is then rotated and/or translated (1020) and a coating is sprayed (1030) on the stent 10 during the rotation (1020). The rotation ratio of the mandrel and stent is 1:1 considering how elements 36 and 42 engage and rotate the stent. Air or gas can be applied (1040) to the stent for drying during and/or subsequent to the application of the coating composition. Acts of spraying and blowing can be repeated if desired (1050). The method 1000 then ends.

Figure 11:
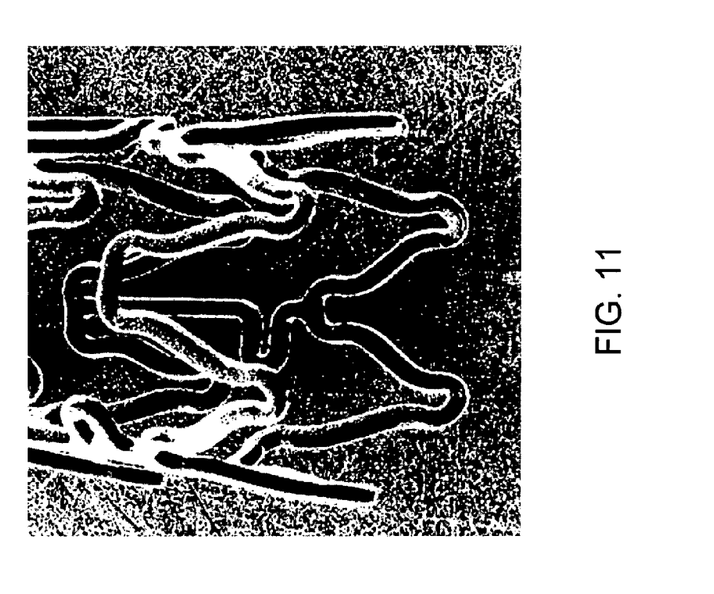
FIG. 11 is a diagram illustrating a stent coated using the stent mandrel fixture of FIG. 3.

FIG. 11 is a diagram illustrating a stent 10 coated using the stent mandrel fixture 20. As can be seen, there are no defects, such as inner diameter tearing, rough surfaces, cob webs, etc., at the end of the stent 10.

The foregoing description of the illustrated embodiments of the present invention is by way of example only, and other variations and modifications of the above-described embodiments and methods are possible in light of the foregoing teaching. For example, the plurality of wires 52 may also be coated with a non-stick polymeric material having less adhesive force with the coating substance than with the members.

What is claimed is:

1. A stent fixture for supporting a stent during formation of a coating, the stent having a first end and an opposed, second end and a bore extending between the first and second ends, the stent fixture comprising:

a first structure having a surface; and a plurality of elongate arm elements extending as cantilevers from the surface and arranged so that the stent fixture is capable of supporting the stent when all of the plurality of arm elements are disposed proximal the first end and distal the second end, extend at least partially through the bore of the stent from the first end and at least a portion of the plurality of arm elements make direct contact with a luminal surface of the stent;

wherein at least a first arm element and a second arm element of the plurality of arm elements extend from the surface at an acute angle relative to each other; and wherein the first structure is configured to support the first end of the stent and wherein the stent fixture additionally comprises a second structure configured to support the second end of the stent.

2. The stent fixture of claim 1, wherein the second structure has a surface and a second plurality of arm elements extending from the second surface and arranged so that the stent fixture is capable of supporting the stent second end when all of the second plurality of arm elements are disposed proximal the second end and distal the first end, extend at least partially through the bore of the stent from the second end and at least a portion of the second plurality of arm elements make direct contact with the luminal surface of the stent.

3. The stent fixture of claim 2, additionally comprising a third structure connecting the first structure to the second structure and configured to extend through the stent bore, wherein the stent can be securely pinched between the first and second plurality of arm elements.

4. The stent fixture of claim 2, wherein each of the first and second plurality of arm elements are configured to extend from their respective surfaces and towards a longitudinal axis of the stent when the stent is supported by the stent fixture.

5. The stent fixture of claim 2, wherein the second plurality of arm elements are parallel to a longitudinal axis of the stent.

6. The stent fixture of claim 2, wherein the second plurality of arm elements include spheres positioned at an end of the arm elements disposed within the bore of the stent when the stent is supported by the stent fixture.

7. The stent fixture of claim 1, further including a first portion of the plurality of arm elements are rigid relative to the stent stiffness such that the first portion is not capable of being deformed when supporting the stent, and a second portion of the plurality of arm elements are flexible relative to the stent stiffness such that the second portion is capable of being deformed when supporting the stent.

8. The stent fixture of claim 1, wherein the first and second arm elements extend out from a perimeter position on the surface and converge towards each other.

9. The stent fixture of claim 1, wherein each of the plurality of arm elements extend from the first side and converge towards each other.

10. The stent fixture of claim 1, wherein each of the plurality of arm elements are supported as cantilevers from the surface.

11. The stent fixture of claim 1, wherein none of the plurality of arm elements contact each other.

12. The stent fixture of claim 11, the plurality of arm elements are rigid relative to the stent stiffness such that each of the plurality of arm elements are not being capable of being deformed when supporting the stent.

13. A stent fixture for supporting a stent during formation of a coating, the stent having a first end and an opposed, second end and a bore extending between the first and second ends, the stent fixture comprising:
    a structure having a surface;
    a plurality of elongate arm elements extending as cantilevers from the surface and arranged so that the stent fixture is capable of supporting the stent when all of the plurality of arm elements are disposed proximal the first end and distal the second end, extend at least partially through the bore of the stent from the first end and at least a portion of the plurality of arm elements make direct contact with a luminal surface of the stent; and
    a mandrel for extending out from the structure and configured to extend at least partially into the stent bore;
    wherein at least a first arm element and a second arm element of the plurality of arm elements extend from the surface at an acute angle relative to each other.

14. The stent fixture of claim 13, wherein the plurality of arm elements converge at an angle towards the mandrel but do not make contact with the mandrel.

15. The stent fixture of claim 13, wherein the plurality of arm elements converge at an angle towards the mandrel and make contact with the mandrel.

16. A stent fixture for supporting a stent during formation of a coating, the stent having a first end and an opposed, second end and a bore extending between the first and second ends, the stent fixture comprising:
    a structure having a surface; and
    a plurality of arm elements extending from the surface and arranged so that the stent fixture is capable of supporting the stent when all of the plurality of arm elements are disposed proximal the first end and distal the second end, extend at least partially through the bore of the stent from the first end and at least a portion of the plurality of arm elements make direct contact with a luminal surface of the stent;
    wherein each of the plurality of arm elements is elongate and orientated such that when the stent fixture is supporting the stent each of the arm elements extend from the surface and into the bore of the stent from the first side;
    wherein each of the plurality of arm elements are supported as cantilevers from the surface;
    wherein each of the plurality of arm elements has a proximal end at the surface, a distal end disposed within the bore of the stent when the stent is supported by the stent fixture, and none of the plurality of arm elements contact each other;
    further including a first portion of the plurality of arm elements are rigid relative to the stent stiffness such that the first portion is not capable of being deformed when supporting the stent, and a second portion of the plurality of arm elements are flexible relative to the stent stiffness such that the second portion is capable of being deformed when supporting the stent.

17. The stent fixture of claim 16, wherein each of the plurality of arm elements have a respective longitudinal axis, and
    wherein at least a first arm element and a second arm element of the plurality of arm elements extend parallel from the surface in such a manner that their respective longitudinal axes extend parallel to each other.

18. The stent fixture of claim 17, wherein a sphere is disposed on each of the distal ends of the plurality of arm elements.

19. A stent fixture for supporting a stent during formation of a coating, the stent having a first end and an opposed, second end and a bore extending between the first and second ends, the stent fixture comprising:
    a structure having a surface; and
    a plurality of arm elements extending from the surface and arranged so that the stent fixture is capable of supporting the stent when all of the plurality of arm elements are disposed proximal the first end and distal the second end, extend at least partially through the bore of the stent from the first end and at least a portion of the plurality of arm elements make direct contact with a luminal surface of the stent;
    wherein each of the plurality of arm elements is elongate and orientated such that when the stent fixture is supporting the stent each of the arm elements extend from the surface and into the bore of the stent from the first side;
    wherein each of the plurality of arm elements are supported as cantilevers from the surface;
    wherein each of the plurality of arm elements has a proximal end at the surface, a distal end disposed within the bore of the stent when the stent is supported by the stent fixture and none of the plurality of arm elements contact each other; and
    wherein each of the plurality of arm elements have a respective longitudinal axis, and wherein at least the first arm element and the second arm element of the plurality of arm elements extend at an acute angle relative to each other such that the respective distal ends are closer to each other than their respective proximal ends.

20. A stent fixture for supporting a stent during formation of a coating, the stent having a first end and an opposed, second end and a bore extending between the first and second ends, the stent fixture comprising:
 a first structure having a surface; and
 a plurality of arm elements extending from the surface and arranged so that the stent fixture is capable of supporting the stent when all of the plurality of arm elements are disposed proximal the first end and distal the second end and extend at least partially through the bore of the stent from the first end;
 wherein at least a portion of the plurality of arm elements extend parallel to each other and include a sphere formed at a respective end proximal a surface of the bore of the stent and distal the surface when the stent is being supported by the stent fixture; and
 wherein the first structure is configured to support the first end of the stent and wherein the stent fixture additionally comprises a second structure configured to support the second end of the stent.

21. The stent fixture of claim 20 wherein the first structure and the second structure have respective first and second surfaces and first and second pluralities of arm elements, wherein the fixture is configured for supporting the stent by suspending the stent from the spheres of the first and second plurality of arm elements.

22. The stent fixture of claim 21 wherein the first and second pluralities of arm elements are arranged to extend approximately parallel to each other and a longitudinal axis of the stent when the stent is being supported by the stent fixture.

23. A stent and a stent fixture supporting the stent, the stent having a first end and an opposed, second end and a bore extending between the first and second ends, comprising:
 a first structure and a second structure having respective first and second surfaces, the first surface being disposed proximal the first end and the second surface being disposed proximal the second end and the stent being supported at its first and second ends by respective first and second plurality of arm elements, each of the first and second plurality of arm elements
 extending from the respective surface and arranged to support the stent by all of the plurality of arm elements being disposed proximal the respective end and extending at least partially through the bore of the stent from the respective end, and
 at least a portion of the plurality of arm elements are selected from the set consisting of
 at least one arm element extending parallel to another arm element and each of the arm elements including a sphere formed at a respective end in contact with the stent bore; and
 for at least one pair of arm elements, each arm element having a distal end disposed within the bore and a proximal end disposed outside the bore, and the arm element distal ends are closer to each other than their proximal ends.

* * * * *